United States Patent [19]
Fröberg et al.

[11] Patent Number: 5,697,804
[45] Date of Patent: Dec. 16, 1997

[54] IMPLANTABLE CARDIAC STIMULATOR HAVING A LOCKING DEVICE FOR RELEASABLY RETAINING A PIN-LIKE ELEMENT OF AN ELECTRODE LEAD

[75] Inventors: Paul Fröberg, Bromma; Kenneth Dahlberg, Stockholm, both of Sweden

[73] Assignee: Pacesetter AB, Solna, Sweden

[21] Appl. No.: 586,192

[22] Filed: Jan. 16, 1996

[30] Foreign Application Priority Data

Jan. 26, 1995 [SE] Sweden ............... 9500273-9

[51] Int. Cl.⁶ .................................. H01R 4/50
[52] U.S. Cl. ................. 439/346; 439/841; 607/37
[58] Field of Search ..................... 439/346, 840, 439/841; 607/2, 9, 37

[56] References Cited

U.S. PATENT DOCUMENTS

| | | | |
|---|---|---|---|
| 2,427,001 | 9/1947 | Hubbell et al. | 439/841 X |
| 3,295,872 | 1/1967 | Kragle. | |
| 3,364,302 | 1/1968 | Slick | 439/841 X |
| 3,885,848 | 5/1975 | Brouneus | 439/841 |
| 4,027,678 | 6/1977 | van Oostveen et al. | |
| 4,620,763 | 11/1986 | Mochida | 439/841 X |
| 5,086,773 | 2/1992 | Ware. | |

FOREIGN PATENT DOCUMENTS 0 448 760   10/1991   European Pat. Off..

*Primary Examiner*—Khiem Nguyen
*Attorney, Agent, or Firm*—Hill, Steadman & Simpson

[57] ABSTRACT

An implantable cardiac stimulator has locking device for a pin-like conductor element of an electrode lead, the locking device having a helical coil which can assume a first, locking position, in which it grips the pin-like conductor element inserted into the coil to prevent longitudinal movement of pin-like conductor element, and a second, release position in which the pin-like conductor element is free to move in and out of the coil in relation to the coil's longitudinal axis. The first position is assumed when the coil is not influenced in its helix diameter increasing direction and the second position being assumed when the coil is influenced in its helix diameter increasing direction. The locking device also has a blocking component which only prevents the coil from rotating in the unwinding direction around its longitudinal axis in the locking device.

10 Claims, 3 Drawing Sheets

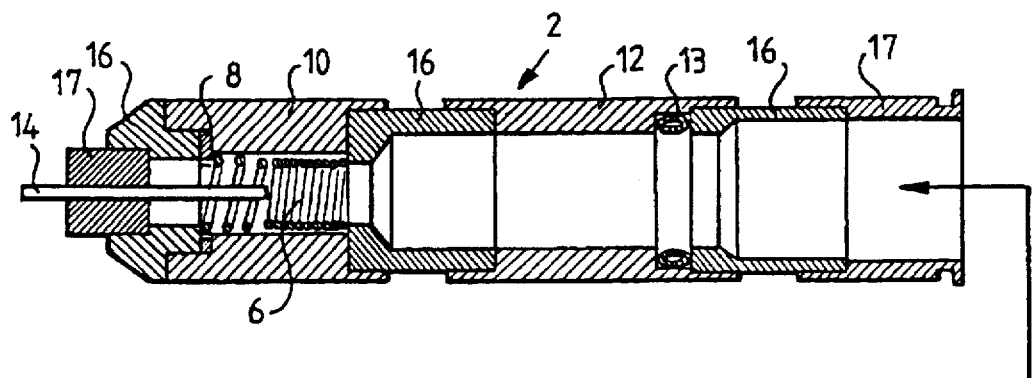
Fig. 1
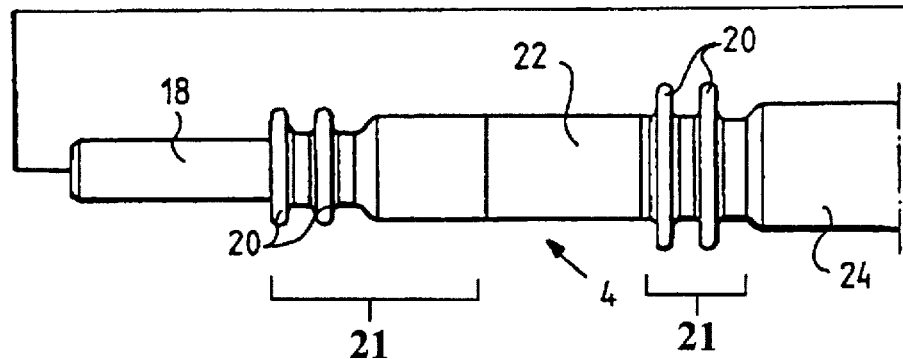
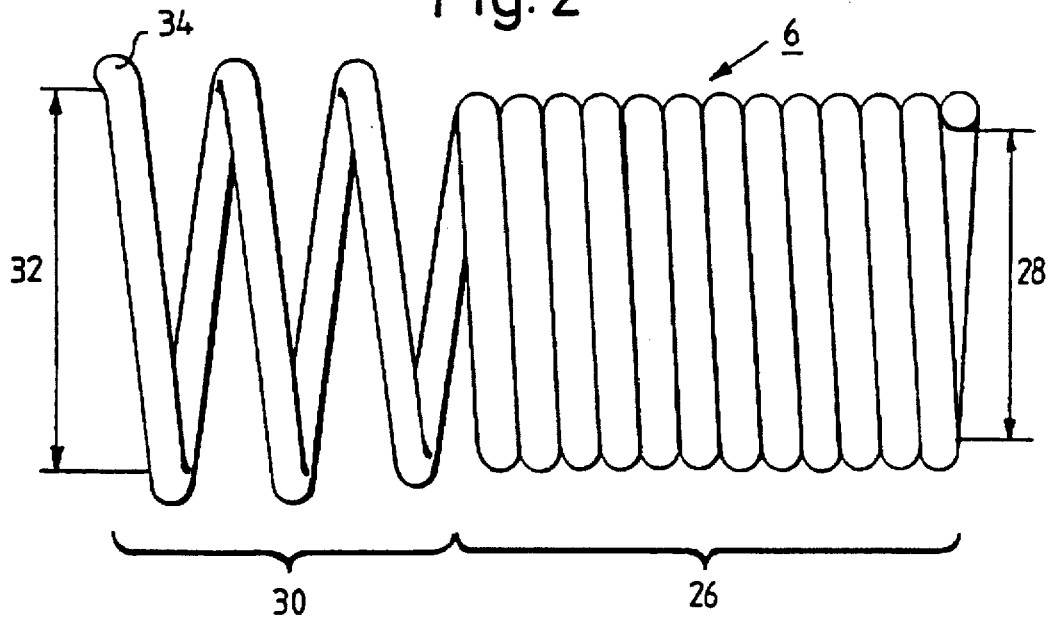
Fig. 2

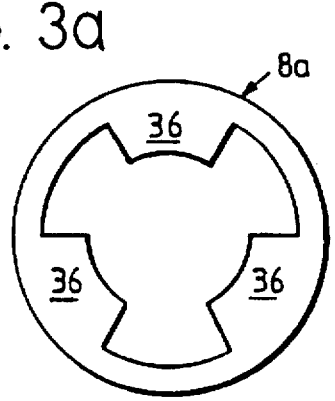
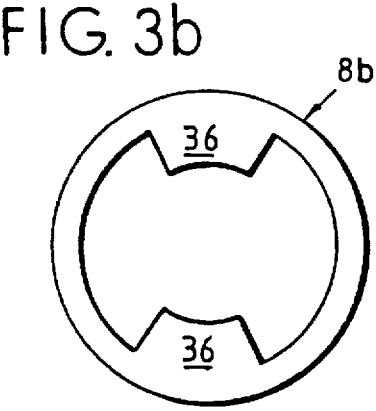
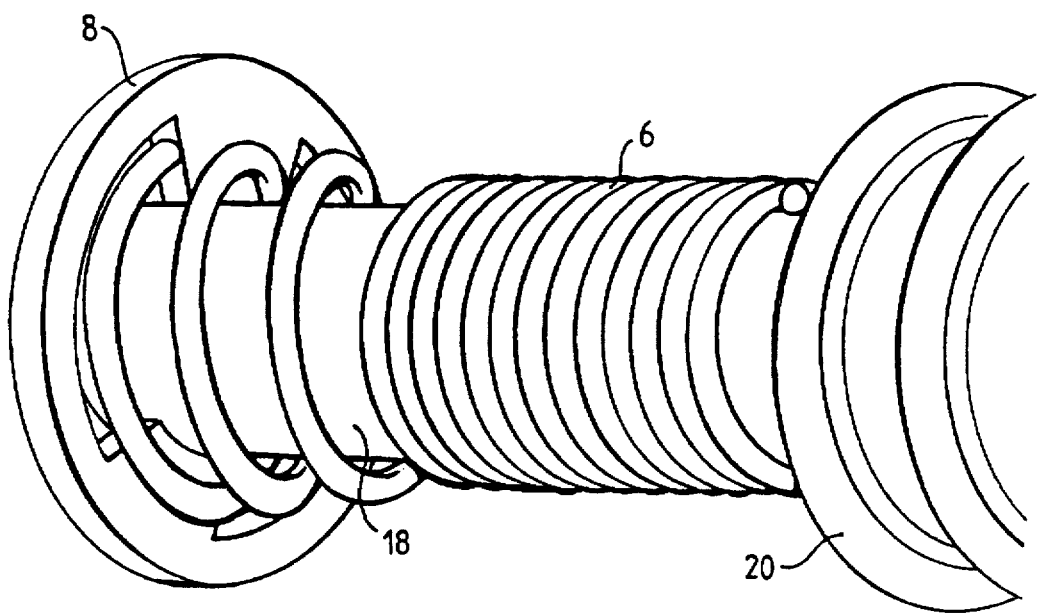

IMPLANTABLE CARDIAC STIMULATOR HAVING A LOCKING DEVICE FOR RELEASABLY RETAINING A PIN-LIKE ELEMENT OF AN ELECTRODE LEAD

BACKGROUND OF THE INVENTION

1. Field of the Invention

The present invention relates to an implantable cardiac stimulator having a locking device of the type having a helical coil which can assume a first, locking position by surrounding and gripping a pin-like element of an electrode lead inserted into the coil to prevent longitudinal movement of the pin-like element, and a second, release position in which the pin-like element is free to move in and out of the coil, the first position being assumed when the coil is not influenced to cause its helical diameter to increase and the second position being assumed when the coil is influenced to cause its helical diameter to increase.

2. Description of the Prior Art

The general object of a locking device of the type described above is to releasably secure (hold) a pin-like element for a device without the use of a tool, such as a screwdriver for securing the pin with a special screw such as a set screw.

A pacemaker connector provides a mechanical connection between an electrode cable terminal and the pacemaker housing and simultaneously makes an electrical connection between the cable terminal which is connected to one or more conductors in the cable and the electronics contained in the housing. Such connectors often include a connector housing with attendant electrode connections, the connector housing being made of a transparent epoxy plastic affixed to the top of the pacemaker capsule. The terminal connections in the connector housing, which contact the cable terminal, are electrically connected to the pacemaker circuits in the capsule via a plurality of connecting leads. The proximal end of the electrode terminal has a contact pin which is secured inside the connector housing with, e.g., screws. U.S. Pat. No. 5,086,773 provides examples of such solutions in its description of the prior art. The device subsequently described in U.S. Pat. No. 5,086,773 is an example of the way the contact pin can be secured without any screws or tools. The locking device described there contains at least one helical coil arranged in a connection receptacle for locking the contact pin. The internal diameter of the coil is somewhat smaller than the external diameter of the contact pin.

When the contact pin is rotated a portion of one revolution in the coil's unwinding direction at the same time as the contact pin is pressed into the connection receptacle, the coil expands enough to admit the contact pin. When the contact pin is released, the coil strives to resume its normal position, with the result that the coil grips the contact pin, thereby locking the electrode cable's contact pin and establishing electrical contact.

European Application 0 448 760 also provides examples of a locking device in which a coil is installed in a connection receptacle, in the same way as in U.S. Pat. No. 5,086,773, to lock and establish electrical contact for a contact pin on an electrical conductor in the connection receptacle.

The innermost end section of the locking coil used in these known devices is mounted in some way in the connection receptacle. A problem with these known devices is that if the contact pin, when locked by the locking device, is inadvertently rotated in the coil's winding direction, i.e., opposite its unwinding direction, the coil might break.

SUMMARY OF THE INVENTION

It is an object of the present invention to provide an implantable cardiac stimulator having a locking device of the type generally described above which avoids the problem in the art of coil breakage if the contact pin is inadvertently rotated in the winding direction of the coil.

The above object is achieved in accordance with the principles of the present invention in an implantable cardiac stimulator having a locking device having a helical coil which can assume a first, locking position, in which it grips a rod or pin of an electrode lead inserted into the coil to prevent longitudinal movement of the rod or pin, and which can also assume a second, release position in which the rod or pin is free to move in and out of the coil, the first position being assumed when the coil is not influenced in its helix diameter increasing direction, and the second position being assumed when the coil is influenced in its helix diameter increasing direction, and the locking device having a blocking component which only prevents the coil from rotating in its unwinding direction around its longitudinal axis.

In the locking device of the invention, if the contact pin, surrounded by the coil, is inadvertently rotated in the winding direction of the coil, the blocking component permits free rotation of the coil with the pin inside the locking device.

Thus, the invention achieves a locking device with a blocking component which only prevents the coil from rotating in its unwinding direction around its longitudinal axis in relation to the locking device, thereby eliminating the problem of broken springs with the known devices.

The locking device is particularly suited for use as a locking device in a connector of a medical implant, such as a pacemaker or a defibrillator, for making an electrical and mechanical connection to the terminal pin of one or more conductors of an electrode cable.

DESCRIPTION OF THE DRAWINGS

FIG. 1 is a sectional view of a locking device constructed in accordance with the principles of the present invention embodied in a connector for a medical implant.

FIG. 2 shows a helical coil used in the locking device of the invention.

FIGS. 3a and 3b respectively show two embodiments of a blocking component according to the invention.

FIG. 4 shows a contact pin affixed by the locking device according to the invention.

DESCRIPTION OF THE PREFERRED EMBODIMENTS

Figure 5:
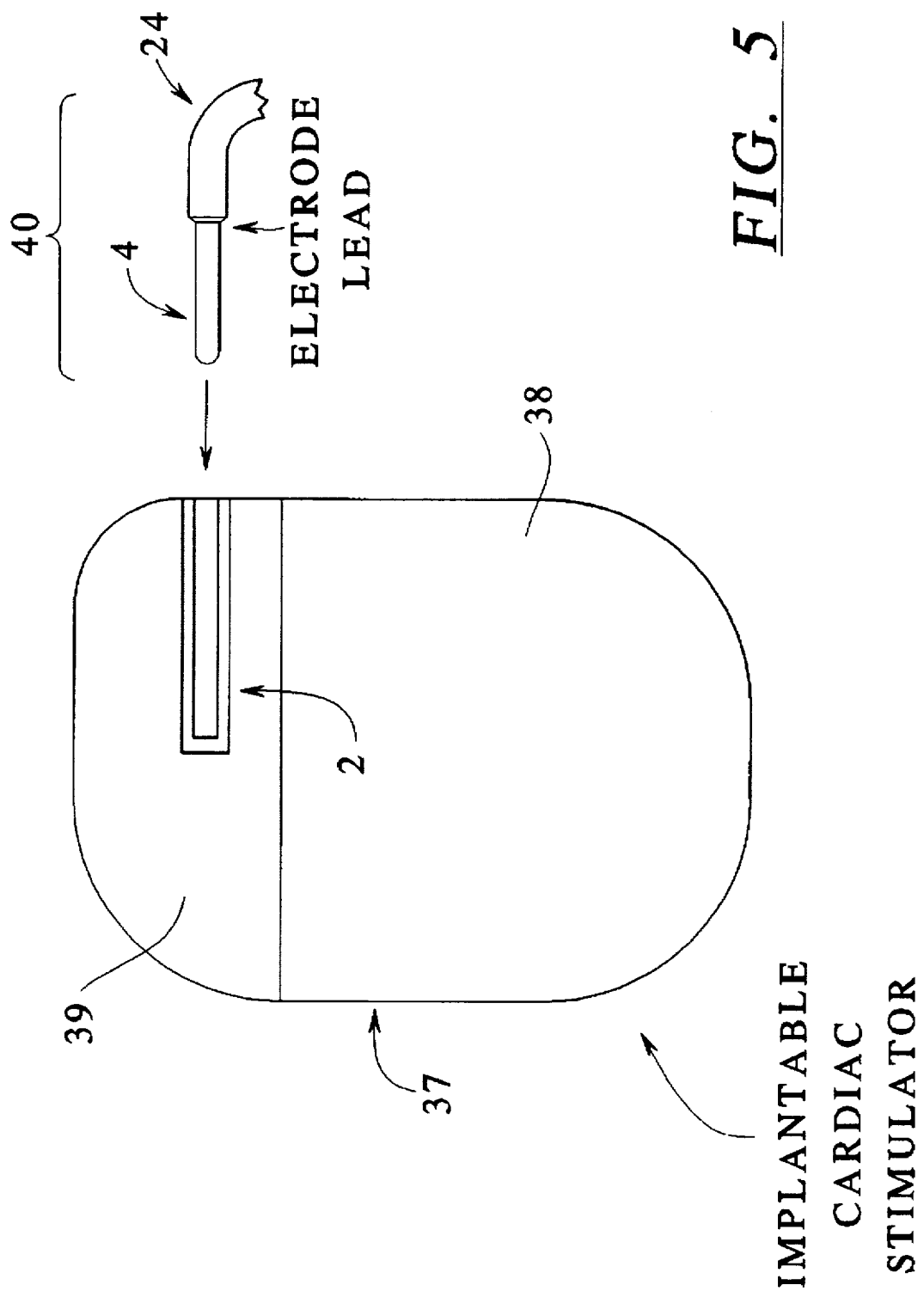
FIG. 5 shows an implantable cardiac stimulator, in the form of a peacemaker, embodying the locking device shown in FIGS. 1–4.

As shown in FIG. 5, an implantable cardiac stimulator 37 has a lower portion 38, commonly made of metal, which contains electronic components, and an upper portion 39, commonly referred to as a "header" and made of transparent plastic, which contains a receptacle having a locking device 2 therein. The receptacle with the locking device 2 therein receives an electrical conductor 4 disposed at the end of an electrode lead 40 (only a portion of which is shown in FIG. 5). The electrode 40 has an insulating cable 24 which contains one or more wire conductors in connection with the electrical conductor 4 so as to deliver stimulation energy in vivo to a heart.

FIG. 1 is a schematic rendition of the according to the invention and the conductor 4 of the lead 40 which is to be held in place by the locking device 2. The locking device 2 has a helical coil 6 and a blocking component 8. The locking device 2 further includes a first contact 10, a second contact 12 with a contact coil 13, a third contact 14, insulating parts 16 and support parts 17. The electrical conductor 4 has a contact pin 18, insulated areas 21 with flanges 20, a contact region 22 the electrical conductor 4 extends from the end of the insulated cable 24. The flanges 20 are made of a resilient material which help secure the electrical conductor 4 in the locking device 2.

FIG. 2 shows the helical coil 6. It has a fixing section 26 in which the coil is tightly coiled in 10–15 turns, preferably 12 turns, with no spacing between turns. The fixing section 26 has a first internal diameter 28 which is slightly smaller than the diameter of the contact pin 18.

After 10–15 turns, the fixing section 26 changes into a pressure section 30 in which the coil 6 is loosely coiled with a greater pitch than in the fixing section 26. The pressure section 30 has fewer turns, i.e. 2–5 turns, preferably 3 turns, than the fixation section 26. The pressure section 30 has a second internal diameter 32 which is slightly larger than the diameter of the contact pin 18. The pressure section 30 terminates with an end section 34.

FIGS. 3a and 3b show two embodiments of the blocking component 8. In both embodiments, the blocking component 8 consists of a washer with a hole in the middle. The diameter of the hole is slightly larger than the external diameter of the pressure section 30. A number of blocking elements 36 are arranged in the center of the washer. FIG. 3a shows a blocking component 8a with two blocking elements 36 and FIG. 3b shows a blocking component 8b having three blocking elements 36. It is, of course, possible to have only one blocking elements 36 is or more than three blocking elements 36, of course. The blocking parts 36 can be described as tabs whose innermost edges, if connected by imaginary arcs, would form a circle with a diameter less than the internal diameter 32 of the pressure section 30 but larger than the diameter 18 of the contact pin.

FIG. 4 shows the contact pin 18 locked in place with the locking device according to the invention.

The functioning of the invention will now be described in greater detail.

The coil spring 6 is constrained under tension inside a space capped by the blocking component 8 at one end and the insulating part 16 nearest the coil 6 at the other end. The blocking component 8 is mounted by a combination of a weld and clamp so that only blocking elements 36 are inside the inner walls of the locking device 2. The coil 6 is arranged so that the pressure section 30 is slightly compressed and so the coil 6, the end section 34 in particular, presses against the blocking elements 36.

When the electrical conductor 4 with the contact pin 18 is to be secured by the locking device 2, it is pressed into the spring 6 at the same time as it is rotated in the unwinding direction, causing the coil 6 to expand by increasing its helix diameter and to assume a release position in relation to its longitudinal axis. The contact pin 18 is inserted into the coil 6 while simultaneously being rotated. Rotating the contact pin 18 less than one revolution is enough to cause expansion of the coil 6. The coil's end section 34 presses against the blocking elements 36 when the contact pin 18 is rotated in the unwinding direction, thereby preventing the spring 6 from rotating more than part of one revolution.

When the coil 6 is not influenced in its helix diameter increasing direction, i.e. when rotation of the contact pin 18 in the unwinding direction ceases and the contact pin 18 has been introduced into the coil 6, the coil 6 assumes a locking position in relation to its longitudinal axis, thereby locking the contact pin 18 in place. When the electrical conductor 4 with the contact pin 18 is to be detached from the locking device 2, the contact pin 18 is rotated in the unwinding direction of the coil 6, i.e. the same rotation direction as in locking, thereby influencing the coil 6 in its helix diameter increasing direction. The coil 6 will then return to its release position in relation to its longitudinal axis and relax its grip on the contact pin 18 which can then be withdrawn.

If the coil 6 with the locked contact pin 18 is rotated in the winding direction of the coil 6, the coil 6 will rotate with the contact pin 18, since the end section 34 will slide over the blocking elements 36, which fail to prevent rotation. This accordingly eliminates the problem of coils being broken by twisting, as has occurred in locking devices with a rigidly mounted coil.

Establishing electrical contact with the electrical conductor 4 is performed by a connection to the first contact 10 to which the blocking component 8 is electrically connected. Since the spring 6 is under tension, it constantly presses against the blocking component 8 and guarantees contact with the contact pin 18 by grip of the fixing section 26 on the contact pin 18. Electrical contact can also be made with the second contact 12 which, via the contact coil 13, presses against the connection 22 on the conductor 4. The third contact 14 consists of a connection pin, concentrically arranged in the locking device 2, which contacts the contact pin 18 when the connection pin is inserted into an opening (not shown) in the contact pin 18. This third contact 14 can be used to indicate that the contact pin has been correctly locked and electrical contact established.

It is within the scope of the invention for the pressure section 30 of the coil 6 to have a conical shape with a first internal diameter 28 in the fixation section 26, this diameter increasing at the transition to the pressure section 30 to a second internal diameter 32 at the end of the pressure section 30.

The terminal part of the pressure section 30 up to the end section 34 can be devised in a number of different ways. For example, it can have a defined bend toward the blocking component 8. Another possibility is for the terminal part of the pressure section 30 up to the end section 34 to have a larger diameter than the rest of the pressure section 30 and to interact with the blocking component 8, which has blocking elements 36 which can consist of notches or grooves on the inside of the locking device 2.

According to the above, the special application of the invention relates to the locking and electrical contact of an electrical conductor for a medical implant. The implant can be a pacemaker or defibrillator. The length of the coil 6 used in this special application is about 3 mm, the first internal diameter 28 being about 1.45 mm and the second internal diameter 32 being about 1.8 mm. The diameter of the contact pin is about 1.6 mm.

According to a second special application of the invention, the locking device is employed to lock and establish electrical contact for a contact pin for an electrical conductor.

According to a third special application of the invention, the locking device is only used for mechanically locking the pin of an apparatus or some other device. Application of the invention would be much easier when locking is the only function of interest, since no consideration need then be given to establishing electrical contact.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable cardiac assist system comprising:

an electrode lead having a pin-like conductor element at one end thereof;

an implantable cardiac stimulator having a receptacle containing a locking device for retaining said pin-like element;

a helical coil in said locking device, having a longitudinal axis, which can assume a locking position in which it grips said pin-like conductor element inserted into said coil for preventing longitudinal movement of the pin-like conductor element, and a release position in which the pin-like conductor element is free to move longitudinally relative to said coil, said locking position being assumed when said coil is not influenced in a helix diameter increasing direction and said release position being assumed when said coil is influenced in said helix diameter increasing direction; and blocking means in said locking device for interacting with said coil for only preventing rotation of said coil in an unwinding direction around said longitudinal axis of said coil.

2. An implantable cardiac assist system as claimed in claim 1 wherein said coil has a tightly coiled fixing section and a loosely coiled pressure section, said pressure section being longitudinally shorter than said fixing section, and said pressure section terminating in an end section which interacts with said blocking means.

3. An implantable cardiac assist system as claimed in claim 2 wherein said fixing section has a fixing section internal diameter and wherein said pressure section has a pressure section internal diameter, said fixing section internal diameter being smaller than said pressure section internal diameter.

4. An implantable cardiac assist system as claimed in claim 2 wherein said blocking means comprises at least one blocking element for interacting with said end section for preventing said coil from rotating in said unwinding direction.

5. An implantable cardiac assist system as claimed in claim 2 wherein said pressure section has an internal diameter which increases from a smallest internal diameter adjacent said fixing section.

6. An implantable cardiac assist system as claimed in claim 4 wherein said pressure section has a plurality of coil flights bent toward said blocking means.

7. An implantable cardiac assist system as claimed in claim 4 wherein a portion of said pressure section has a larger diameter than a remainder of said pressure section, and said blocking means comprising an annular component having a plurality of notches therein respectively interacting with said end of said pressure section.

8. An implantable cardiac assist system as claimed in claim 1 wherein said coil is adapted for assuming said locking and release positions relative to a contact pin of an electrical conductor comprising said pin-like conductor element.

9. An implantable cardiac assist system as claimed in claim 1 wherein said coil is adapted to assume said locking and release positions relative to a contact pin connected to an electronic apparatus comprising said pin-like conductor element.

10. An implantable cardiac assist system as claimed in claim 1 wherein said coil is adapted for assuming said locking and release positions relative to a terminal pin of an electrode lead of a medical implant comprising said pin-like conductor element.

* * * * *